(12) United States Patent
Artico et al.

(10) Patent No.: US 8,765,150 B2
(45) Date of Patent: Jul. 1, 2014

(54) RILUZOLE AQUEOUS SUSPENSIONS

(75) Inventors: Roberta Artico, Milan (IT); Marco Adami, Milan (IT); Daniele Barbareschi, Milan (IT); Jaime Moscoso, Alcoendas (ES); Tiziano Oldoni, Milan (IT); Paolo Mascagni, Milan (IT)

(73) Assignee: Italfarmaco SpA, Milan (IT)

( * ) Notice: Subject to any disclaimer, the term of this patent is extended or adjusted under 35 U.S.C. 154(b) by 0 days.

(21) Appl. No.: 13/138,047

(22) PCT Filed: Mar. 2, 2010

(86) PCT No.: PCT/EP2010/052598
§ 371 (c)(1),
(2), (4) Date: Nov. 3, 2011

(87) PCT Pub. No.: WO2010/102923
PCT Pub. Date: Sep. 16, 2010

(65) Prior Publication Data
US 2012/0039953 A1 Feb. 16, 2012

(30) Foreign Application Priority Data
Mar. 13, 2009 (EP) .................................. 09425101

(51) Int. Cl.
*A61K 31/428* (2006.01)
*A61P 25/00* (2006.01)
*A61K 9/14* (2006.01)

(52) U.S. Cl.
USPC .......................................... 424/400; 514/367

(58) Field of Classification Search
CPC .................. A61K 47/20–47/34; A61K 9/0095
USPC .......................................... 424/400; 514/367
See application file for complete search history.

(56) References Cited

U.S. PATENT DOCUMENTS

| | | | |
|---|---|---|---|
| 5,360,817 A | 11/1994 | von Izstein et al. | |
| 5,527,814 A | 6/1996 | Louvel | |
| 6,194,000 B1 * | 2/2001 | Smith et al. | 424/458 |
| 6,387,936 B1 | 5/2002 | Blanchard-Bregeon et al. | |
| 6,613,308 B2 * | 9/2003 | Bartus et al. | 424/45 |
| 6,861,413 B2 * | 3/2005 | Li et al. | 514/29 |
| 2002/0037902 A1 | 3/2002 | Aubourg et al. | |
| 2003/0077297 A1 * | 4/2003 | Chen et al. | 424/400 |
| 2003/0180352 A1 * | 9/2003 | Patel et al. | 424/465 |
| 2004/0127577 A1 | 7/2004 | Blaugrund et al. | |
| 2005/0266032 A1 | 12/2005 | Srinivasan et al. | |
| 2006/0057205 A1 | 3/2006 | Srinivasan et al. | |
| 2006/0165807 A1 | 7/2006 | Castan et al. | |
| 2006/0233831 A1 * | 10/2006 | Parisot et al. | 424/204.1 |
| 2007/0190043 A1 * | 8/2007 | Sych et al. | 424/130.1 |
| 2008/0194532 A1 * | 8/2008 | Rabinovich-Guilatt et al. | 514/182 |

FOREIGN PATENT DOCUMENTS

| | | | |
|---|---|---|---|
| WO | WO 00/74676 A1 | 12/2000 | |
| WO | WO 01/11964 A1 | 2/2001 | |
| WO | WO 2004/096216 A2 | 11/2004 | |
| WO | WO 2005/084377 A2 | 9/2005 | |
| WO | WO 2008/000448 A2 | 1/2008 | |

* cited by examiner

*Primary Examiner* — Richard Schnizer
*Assistant Examiner* — Alma Pipic
(74) *Attorney, Agent, or Firm* — Nixon & Vanderhye, P.C.

(57) ABSTRACT

Physically and chemically stable aqueous oral suspensions of riluzole and manufacturing methods thereof. The suspensions contain riluzole in particle form and at least a wetting agent, preferably a surfactant. Riluzole is present in amounts from about 0.1% to about 20% w/v and has an average particle size lower than 200 μm. The suspensions are devoid of the known local (mouth) anaesthetic effects of riluzole.

18 Claims, No Drawings

RILUZOLE AQUEOUS SUSPENSIONS

This application is the U.S. national phase of International Application No. PCT/EP2010/052598 filed 2 Mar. 2010 which designated the U.S. and claims priority to European Application No. 09425101.4 filed 13 Mar. 2009, the entire contents of each of which are hereby incorporated by reference.

The present invention relates to physically and chemically stable oral aqueous suspensions of riluzole for oral administration, having minimal or no anaesthetic effect in the mouth.

BACKGROUND OF THE INVENTION

Riluzole (6-(trifluoromethoxy)benzothiazol-2-amine) is a compound of formula

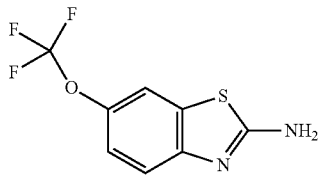 [SMILES: Nc1nc2ccc(OC(F)(F)F)cc2s1]

Riluzole, a drug used to treat amyotrophic lateral sclerosis (ALS, sometimes called Lou Gehrig's disease, Maladie de Charcot or motor neurone disease), is usually administered in an oral form at the dose of 50 mg every 12 hours and it delays the onset of ventilator-dependence or tracheostomy in selected patients.

ALS is a progressive, fatal neurodegenerative disease caused by the degeneration of motor neurons. It is marked by gradual degeneration of the central nervous system nerve cells that control voluntary muscle movement. As motor neurons degenerate, they can no longer send impulses to the muscle fibers that normally result in muscle movement. Early symptoms of ALS often include increasing muscle weakness, especially involving the arms and legs, speech, swallowing or breathing. Riluzole is approved in the US and Europe for treating ALS.

U.S. Pat. No. 5,527,814 discloses the use of riluzole for treating ALS; the riluzole-based formulations exemplified in this patent are a tablet, a hard gelatine capsule and an injectable solution.

U.S. Pat. No. 6,432,992 discloses the use of riluzole for the treatment of adrenoleukodystrophy; also the riluzole-based formulations exemplified in this patent are a tablet, a hard gelatine capsule and an injectable solution.

Oral Riluzole is commercially available as capsule-shaped, white, film-coated tablets containing 50 mg active. Currently there are no commercially available liquid formulations of riluzole.

As opposed to tablets, an oral liquid formulation would increase ALS patients compliance when difficulties in swallowing arise.

Riluzole has a very low solubility in water, about 0.3 mg/mL at neutral pH. Although under acidic conditions the solubility of Riluzole increases and at pH 1.2 is about 12 mg/mL, its chemical stability decreases dramatically. So aqueous acidic solutions for oral use are not feasible.

Nevertheless, it is possible to prepare aqueous solutions having concentrations of riluzole between 0.25 and 10% w/v that are not only technically feasible (for example by using co-solvents or solubilizers to increase riluzole aqueous solubility) but also physically and chemically stable. These solutions, however, exhibit very poor palatability due to a significant and persistent (lasting more than 20-30 minutes) anesthetic effect in the mouth, which is due to the intrinsic property of the drug itself.

Due to its lipophilic character and Its low water solubility, riluzole is a good candidate for a suspension formulation.

DESCRIPTION OF THE INVENTION

Suspensions are dispersed, two-phase systems, in which one phase ("internal" phase) particles are dispersed in the second phase ("continuous" or "external" phase). As such, they are by definition thermodynamically unstable and tend to revert to an energetically more stable state by for example undergoing aggregation, sedimentation, crystal growth and caking.

A suspension contains solid particles dispersed in a liquid or semisolid medium. As suspensions are thermodynamically unstable, the dispersed particles tend to aggregate and/or to sediment in order to reduce the surface area. To minimise the settling of the dispersed particles and to prevent caking of sedimented particles two are the key requirements in suspension formulation. The most common way is the controlled flocculation approach. Flocculation is the process where suspended particles agglomerate to form loosely structured flocs, which are held together in a network-like structure. Flocculated particles are therefore weakly bonded. As such they do not form a cake and are easily re-suspended. Nevertheless, which excipients will be successful in stabilizing a suspension is not predictable and their choice is critical to the physical stability of a suspension.

In the present invention, we have surprisingly found that by using certain specific excipients orally administrable aqueous suspensions of riluzole are obtained, which have minimal or no anaesthetic effect at all in the mouth, thus resulting in improved patient compliance.

These aqueous suspensions are physically and chemically stable, which is an essential requirement for industrial preparation and distribution of the corresponding pharmaceutical formulations.

On the other hand, these suspensions are feasible in a wide range of riluzole concentrations, e.g., from 0.1% to more than 15% (w/v). This provides the doctors with different dosage and administration regimens, permits to personalize the treatment and, therefore, improves patient compliance.

Accordingly, a first aspect of the invention relates to stable aqueous suspensions containing riluzole with minimal or no anaesthetic effect in the mouth. The suspension of the present invention is thus preferably administered orally; nevertheless, such a suspension may enable the enteric nutrition of those ALS patients, who, due to their reduced mobility, require additional routes of feeding.

In a second aspect the invention relates to said suspensions of riluzole for use in the treatment of ALS.

In a third aspect the invention relates to method(s) of preparation of these suspensions of riluzole.

Accordingly, the first embodiment of the invention relates to aqueous suspensions comprising particles of riluzole or a pharmaceutically acceptable salt or derivative thereof and at least a wetting agent.

Preferably, the amount of riluzole or said pharmaceutically acceptable salt or derivative thereof is from about 0.1% to about 20% w/v. In a more preferred embodiment, riluzole is present in amounts from about 0.2% to about 10% w/v, preferably from about 0.3 to about 6% w/v.

For the purposes of the present invention, the expression "w/v" is intended to indicate the weight of the mentioned compound (in g) with respect to the volume of the whole suspension (per 100 ml).

Preferably the average particle size of riluzole should be lower than 200 μm. In a more preferred embodiment the particle size is from about 75 μm to about 25 μm, more preferably, from about 50 μm to about 10 μm.

For the purposes of the present invention the term "wetting agent" is intended to indicate a substance that promotes the proper wetting of a hydrophobic material, e.g., by lowering the interfacial tension and contact angle between solid particles and liquid vehicle, as for instance disclosed in Pharmaceutical Dosage Forms, Disperse Systems, Volume 1, edited by H. A. Lieberman, M. M. Rieger, and G. S. Banker, 1988 by Marcel Dekker, New York and Basel.

According to a preferred embodiment of the invention, the wetting agent is at least one surfactant, preferably selected from: anionic surfactants, non-ionic surfactants and combinations thereof.

Preferably the wetting agent is present in amounts from about 0.005% to about 2% w/v, more preferably from about 0.01% to about 0.5% w/v.

Suitable surfactants for the present invention may be selected from carboxylates, natural emulsifiers (e.g., phospholipids), esters of sulphuric acid (e.g., alkyl sulfates), sulfonates, non-ionic ethers (e.g., fatty alcohol ethoxylates, propoxylated alcohols, ethoxylated/propoxylated block polymers).

Preferably the surfactant is selected from the group of sodium lauryl sulphate (SLS), dioctyl sodium sulfosuccinate (or sodium docusate, DSS), polyoxyethylene castor oil derivatives (sold under Cremophor® trademark), polyoxyethylene fatty ethers (or ethoxylated fatty alcohols, sold under Volpo® trademark) and poloxamers.

According to an embodiment, the anionic surfactant is selected from:
  sodium lauryl sulphate (in amounts from about 0.0001% to about 1% w/v, preferably from about 0.0005 to about 0.5% w/v, more preferably from about 0.001 to about 0.1% w/v);
  sodium docusate (in amounts from about 0.0001% to about 1% w/v, preferably from about 0.0005 to about 0.5% w/v, more preferably from about 0.001 to about 0.1% w/v).

According to another embodiment, the non ionic surfactant is a polyoxylated oil and/or a polyethylenglycol (PEG) ether; said non ionic surfactant being preferably selected from:
  polyoxyl 35 castor oil, such as Cremophor® EL, or polyoxyl 40 hydrogenated castor oil, such as Cremophor® RH 40 (in amounts from about 0.01% to about 2% w/v, preferably from about 0.05% to about 0.75% w/v, more preferably from about 0.1% to about 0.3% w/v);
  PEG 25 cetostearyl ether, such as Volpo® CS 25 (in amounts from about 0.01% to about 2% w/v, preferably from about 0.05 to about 0.75% w/v, more preferably from about 0.075% to about 0.3% w/v);
  PEG 5 oleyl ether, such as Volpo® N5 (in amounts from about 0.01% to about 2% w/v, preferably from about 0.05 to about 0.75% w/v, more preferably from about 0.075% to about 0.3% w/v).

Surprisingly, the present inventors have found that ethoxylated fatty alcohols lead to stable suspensions even at concentrations of riluzole as low as 0.5% w/v. This is surprising because stable suspensions with concentrations of the active principle lower than 1.0% w/v are normally difficult to obtain even with active principles other than riluzole.

Accordingly, a preferred embodiment of the present invention relates to stable suspensions of riluzole comprising at least one surfactant selected from ethoxylated fatty alcohols and riluzole or a pharmaceutically acceptable salt or derivative thereof and wherein riluzole or said pharmaceutically acceptable salt or derivative thereof is in amounts lower than 1.0%, w/v preferably from 0.3% to 0.8% w/v.

On the other hand, the present inventors have also surprisingly found that the combination of two different surfactants, preferably a ionic surfactant and a non-ionic surfactant, results in an improved physical stability of the suspension. This is surprising because a surfactant usually acts as a wetting agent and it is well established that only minimal quantities of wetting agent are needed to produce an adequate dispersion of the particles. In contrast, increasing the concentration of the surfactant (by for instance adding a second such an agent) might generate deflocculation of the dispersed particles.

The inventors have thus found that suspensions of riluzole in the presence of two different surfactants, preferably a ionic surfactant and a non-ionic surfactant have a high degree of flocculation, instead of undergoing deflocculation as expected by the increased concentration of the wetting agents.

Accordingly, a preferred embodiment of the present invention relates to stable compositions of riluzole comprising particles of riluzole or a pharmaceutically acceptable salt or derivative thereof and at least two surfactants, preferably a ionic surfactant and a non-ionic surfactant. The ionic surfactant is preferably selected from sodium lauryl sulphate and sodium docusate whereas the non-ionic surfactant is preferably selected from polyethylenglycol ethers (also called ethoxylated fatty alcohols) such as PEG 25 cetostearyl ether. The combination of two different surfactants results to be particularly preferred when riluzole or said pharmaceutically acceptable salt or derivative thereof are used in amounts lower than 10% w/v, preferably lower than 5% w/v, more preferably from about 0.3% to about 4.0% w/v.

Preferably the suspensions of the present invention include a suspending agent. For the purposes of the present invention the term "suspending agent" is intended to indicate a substance that impart viscosity and/or act as protective colloids, thus resulting in a stable dispersion, in that they retard settling and agglomeration of the particles, as for instance disclosed in Pharmaceutical Dosage Forms, Disperse Systems, Volume 1, edited by H. A. Lieberman, M. M. Rieger, and G. S. Banker, 1988 by Marcel Dekker, New York and Basel.

The preferred suspending agents are selected from the group of smectite clays, xanthan gum, agar-agar, alginates, tragacanth gum, guar gum, and other natural gums, microcrystalline cellulose and their combinations.

Smectite clays according to the invention is preferably magnesium aluminium silicate (MAS; sold under trademark Veegum®).

In a more preferred embodiment the suspending agent is selected from:
  xanthan gum (in amounts from about 0.1% to about 3.0% w/v, more preferably from about 0.15% to about 1.0% w/v), alone or in admixture with another suspending agent selected from hydroxypropylmethylcellulose (HMPC), sodium carboxymethyl-cellulose (NaCMC), methylcellulose (MC), and hydroxyethylcellulose (HEC), (in amounts from about 0.025% to about 4% w/v);
  magnesium aluminium silicate, such as Veegum® (in amounts from about 0.2% to about 5.0% w/v, more preferably from about 0.5 to about 2.0% w/v), either alone or in admixture with another suspending agent selected from hydroxypropylmethylcellulose (HMPC), sodium carboxymethyl-cellulose (NaCMC), methylcellulose (MC), and hydroxyethylcellulose (HEC), in amounts from about 0.025% to about 4% w/v) or with xanthan gum (in amounts from about 0.025% to about 1.0% w/v);

tragacanth gum (in amounts from about 0.2% to about 5.0% w/v, preferably from about 0.5% to about 1.5% w/v).

Either of these suspending agents are added in an amount enough to obtain a viscosity which is sufficiently high to retard sedimentation of the suspended particles but, at the same time, not too high to make dispensing of the liquid dose difficult. Preferably, the suspending agent of the invention is present in amounts from about from 0.1% to about 5% w/v, preferably from about 0.01% to about 2.0% w/v.

The suspending agents usually exhibit plastic, or pseudoplastic, or thixotropic flow or combinations thereof. This is instrumental to physical stability because they have relatively high viscosity under static conditions and therefore sedimentation is retarded, and flow easily at relatively high shear rates (for instance upon agitation), thus permitting easy dispensing from the bottle or vial containers. The viscosity of these systems may typically vary from about 200 mPa·sec. to about 3,000 mPa·sec., depending on the amount and physical grade of the suspending agents. However, more important than the absolute viscosity, is the ease of resuspendability of the system upon gentle manual agitation and the no-caking effect even after prolonged period of storage.

The inventors of the present invention have also surprisingly found that specific combinations of at least one surfactant and at least one suspending agent result in improved physical stability, i.e., improved flocculation.

Accordingly, another preferred embodiment of the present invention relates to stable suspensions of riluzole comprising at least one surfactant selected from ethoxylated fatty alcohols and/or sodium lauryl sulphate, and at least one suspending agent selected from xanthan gum, magnesium aluminium silicate, hydroxypropylmethylcellulose, and/or sodium carboxymethyl-cellulose.

The suspensions of the present invention may also include a preservative.

The preservative may be any pharmaceutically acceptable antimicrobial agent. Preferably it is selected from the group of methylparaben, ethylparaben, propylparaben, butylparaben, benzoic acid, sorbic acid, sodium benzoate, benzyl alcohol, phenylethanol, and mixtures thereof.

In a particularly preferred embodiment the preservative is a mixture of methyl and propylparaben or benzyl alcohol.

The preservative is added in an amount enough to obtain an acceptable antimicrobial capacity. Preferably it is in amounts from about 0.05% to about 2% w/v.

The suspensions of the present invention may also include at least one of the following excipients in amounts known by a skilled in the art:
a density-imparting agent (e.g., sorbitol, xylitol, etc.);
a sweetening agent and/or a flavouring agent;
a humectant/moistener, such as glycerol or propylene glycol;
an anti-foam (e.g., simethicone emulsion).

The suspensions according to the present invention can be prepared following any known process of the prior art. The present invention comprises therefore any method for manufacturing the suspensions of riluzole of the present invention.

In a particular embodiment a suspension according to the present invention can be prepared according to the following steps:

A) Preparation of the Dispersing Vehicle
(a) In a suitable vessel (e.g., jacketed stainless steel tank with stirrer), dissolve the preservative system in about 60-90% of the total available amount of purified water, under stirring (and heating, if required).
(b) Add the prescribed amount of suspending agent and, under stirring, give the material the necessary time to hydrate, i.e., to uniformly disperse/dissolve to give a colloidal dispersion/solution, providing the required viscosity. This step can require heating of the vehicle (e.g., 40-90° C.), in order to facilitate the hydration process. Also, a moistening agent (e.g., glycerol) can be used to facilitate the dispersion of the suspending agent: an intimate and uniform mixture of the moistener and the suspending agent is first prepared, which is then added to the aqueous vehicle. This facilitates the hydration process, because the intimate mixture of the "rigid", high molecular weight polymer with the moistening agent (which is highly hydrophilic and water soluble) exposes a hydrophilic surface to the aqueous vehicle.
(c) The density-imparting agent is added thereto, if required, and the mixture is stirred until dissolution.
(d) Bring the vehicle to room temperature (if necessary).

According to an alternative embodiment, the order of addition of phase (b) and (c) can be inverted (i.e., the hydration of the suspending agent can be accomplished in the aqueous vehicle also containing the density-imparting agent).

B) Pre-Dispersion (Wetting) of Riluzole
(e) In a suitable container add about 5-30% of the total available amount of purified water and disperse under stirring the anti-foam agent, then add under stirring the wetting agent(s) and keep on stirring until dissolved or thoroughly dispersed; then add the prescribed amount of riluzole and stir until a homogeneous, lump-free slurry is obtained.

C) Preparation of the Final Suspension
(f) Add the riluzole pre-dispersion to the dispersing vehicle, under vigorous stirring, and keep on stirring until a homogeneous dispersion is obtained.
(g) Add the sweetening agent(s) and/or the flavouring agent (s), if required, under stirring.
(h) Add purified water q.s. to final volume and stir.
(i) Homogenize the final suspension through a suitable homogenizer (e.g., colloid mill, piston-type, ultraturrax-type, etc.).
(j) Distribute the prescribed volume of suspension into individual primary containers (glass or plastic) and cap.

According to an alternative embodiment, the whole vehicle can be prepared (i.e., the aqueous vehicle containing all components except riluzole) and the active ingredient then added slowly to the vehicle, under stirring.

Possible pharmaceutical suspensions of the invention are provided in the attached examples which, however, are only intended to illustrate and not to limit the invention.

EXAMPLES

For the purposes of the present invention the stability of liquid compositions of riluzole with excipients of different chemical nature, used alone or in combination, was measured.

The suspensions were prepared as reported above, using an ultraturrax-type homogenizer.

The physical stability of the suspensions was verified by the following techniques: appearance (by visual inspection);

degree of flocculation [by determining the sedimentation volume, F, defined as the ratio of the final, or ultimate, volume (or height) of the sediment, $V_u$ (or $H_u$) to the original volume (or height) of the suspension, $V_0$, (or $H_0$), before settling, thus: $F=V_u/V_0$ (or $H_u/H_0$]; optical microscopy (to determine particle size distribution and verify whether or not crystal growth would occur); resuspendability (by gentle manual shaking); viscosity (by means of a rotational rheometer). The chemical stability of suspensions was assessed by means of a specific and stability indicating HPLC method.

The following examples are intended to illustrate the scope of the present invention in all its aspects but not to limit it thereto.

Example 1

Oral Suspension—Riluzole 5.5% (w/v)

| Ingredient | Quantity (mg) |
|---|---|
| Riluzole | 55 |
| Methyl paraben | 1.485 |
| Propyl paraben | 0.165 |
| Sucrose | 440 |
| Glycerol | 27.5 |
| Tragacanth gum | 3.3 |
| Sodium lauryl sulphate | 1.65 |
| Purified water | q.s. to 1 ml |

Manufacturing Method:

(a) Put about 60-90% of the total available amount of purified water into a suitable jacketed stainless steel tank with stirrer and heat to about 70°-90° C. Add the preservative system (methyl paraben and propyl paraben) and stir until dissolved.

(b) While maintaining the temperature at 70°-90° C., add under stirring tragacanth gum, previously intimately dispersed in the prescribed amount of glycerol. Let the gum hydrate, until a homogeneous system is obtained.

(c) Add the prescribed amount of sucrose, and keep on stirring at 70°-90° C., until dissolved.

(d) Bring the vehicle to room temperature, under stirring.

(e) In a separate suitable container prepare the pre-dispersion of riluzole: in about 5-30% of the total available amount of purified water add under stirring the prescribed amount of sodium lauryl sulphate, until dissolved, then add prescribed amount of riluzole under stirring and keep on stirring a homogeneous, lump-free slurry is obtained.

(f) Add the riluzole pre-dispersion to the vehicle, under vigorous stirring, and keep on stirring until a homogeneous dispersion is obtained.

(g) Add purified water q.s. to final volume and stir.

(h) Homogenize the final suspension through a suitable homogenizer (e.g., colloid mill, piston-type, ultraturrax-type, etc.).

(i) Distribute the prescribed volume of suspension into individual primary containers (glass or plastic) and cap.

Stability: this formulation proved to be physically and chemically stable for at least 1 month at 40° C.

Example 2

Oral Suspension—Riluzole 5.5% (w/v)

| Ingredient | Quantity (mg) |
|---|---|
| Riluzole | 55 |
| Methyl paraben | 1.485 |
| Propyl paraben | 0.165 |
| Sucrose | 440 |
| Xanthan gum | 2.75 |
| HPMC | 2.75 |
| Sodium lauryl sulphate | 0.55 |
| Purified water | q.s. to 1 ml |

Stability: this formulation proved to be physically stable for at least 1 week at 40° C.

Example 3

Oral Suspension—Riluzole 2.75% (w/v)

| Ingredient | Quantity (mg) |
|---|---|
| Riluzole | 27.5 |
| Sodium Benzoate | 1.1 |
| Sodium Saccharine | 1.1 |
| Xanthan Gum | 2.75 |
| HPMC | 2.75 |
| Sodium lauryl sulphate | 0.11 |
| Sodium Docusate | 0.275 |
| Simethicone emulsion | 0.11 |
| Purified water | q.s. to 1 ml |

Stability: this formulation proved to be physically and chemically stable for at least 1 week at 40° C.

Example 4

Oral Suspension—Riluzole 2.75% (w/v)

| Ingredient | Quantity (mg) |
|---|---|
| Riluzole | 27.5 |
| Methyl paraben | 1.485 |
| Propyl paraben | 0.165 |
| Sorbitol | 440 |
| Magnesium aluminium silicate (Veegum ® K) | 11 |
| NaCMC | 2.2 |
| Sodium lauryl sulphate | 0.11 |
| PEG 25 cetostearyl ether (Volpo ® CS 25) | 0.11 |
| Simethicone emulsion | 0.11 |
| Purified water | q.s. to 1 ml |

Stability: this formulation was found to be chemically and physically stable for at least 1 month at 40° C./75% R.H.

Example 5

Oral Suspension—Riluzole 2.5% (w/v)

| Ingredient | Quantity (mg) |
| --- | --- |
| Riluzole | 25 |
| Methyl paraben | 1.35 |
| Propyl paraben | 0.15 |
| Sorbitol | 400 |
| Magnesium aluminium silicate (Veegum ® K) | 10 |
| Xanthan gum | 1 |
| Sodium lauryl sulphate | 0.1 |
| PEG 25 cetostearyl ether (Volpo ® CS 25) | 1 |
| Simethicone emulsion | 0.033 |
| Sodium saccharine | 1 |
| Mint flavour | 10 |
| Purified water | q.s. to 1 ml |

Stability: this formulation was found to be chemically and physically stable for at least 1 month at 40° C./75% R.H.

Example 6

Oral Suspension—Riluzole 2.5% (w/v)

| Ingredient | Quantity (mg) |
| --- | --- |
| Riluzole | 25 |
| Methyl paraben | 1.35 |
| Propyl paraben | 0.15 |
| Sorbitol | 400 |
| Magnesium aluminium silicate (Veegum ® HV) | 10 |
| Xanthan gum | 1 |
| Sodium lauryl sulphate | 0.1 |
| PEG 25 cetostearyl ether (Volpo ® CS 25) | 1 |
| Simethicone emulsion | 0.033 |
| Sodium saccharine | 1 |
| Mint flavour | 10 |
| Purified water | q.s. to 1 ml |

Stability: this formulation was found to be chemically and physically stable for at least 1 month at 40° C./75% R.H.

Example 7

Oral Suspension—Riluzole 0.5% (w/v)

| Ingredient | Quantity (mg) |
| --- | --- |
| Riluzole | 5 |
| Methyl paraben | 1.35 |
| Propyl paraben | 0.15 |
| Sorbitol | 400 |
| Magnesium aluminium silicate (Veegum ® HV) | 10 |
| Xanthan gum | 1 |
| Sodium lauryl sulphate | 0.02 |
| PEG 25 cetostearyl ether (Volpo ® CS 25) | 1 |
| Simethicone emulsion | 0.033 |
| Sodium saccharine | 1 |
| Mint flavour | 10 |
| Purified water | q.s. to 1 ml |

Stability: this formulation was found to be chemically and physically stable for at least 1 month at 40° C./75% R.H.

Example 8

Oral Suspension—Riluzole 0.5% (w/v)

| Ingredient | Quantity (mg) |
| --- | --- |
| Riluzole | 5 |
| Methyl paraben | 1.35 |
| Propyl paraben | 0.15 |
| Sorbitol | 400 |
| Magnesium aluminium silicate (Veegum ® K) | 10 |
| Xanthan gum | 1 |
| Sodium lauryl sulphate | 0.02 |
| PEG 25 cetostearyl ether (Volpo ® CS 25) | 1 |
| Simethicone emulsion | 0.033 |
| Sodium saccharine | 1 |
| Mint flavour | 10 |
| Purified water | q.s. to 1 ml |

Stability: this formulation was found to be chemically and physically stable for at least 1 month at 40° C./75% R.H.

Example 9

Oral Suspension—Riluzole 0.5% (w/v)

| Ingredient | Quantity (mg) |
| --- | --- |
| Riluzole | 5 |
| Sorbitol | 400 |
| Magnesium aluminium silicate (Veegum ® HV) | 10 |
| Xanthan gum | 1 |
| Sodium lauryl sulphate | 0.02 |
| PEG 25 cetostearyl ether (Volpo ® CS 25) | 1 |
| Simethicone emulsion | 0.033 |
| Sodium saccharine | 1 |
| Purified water | q.s. to 1 ml |

Stability: this formulation was found to be chemically and physically stable for at least 1 month at 40° C./75% R.H.

Example 10

Oral Suspension—Riluzole 0.5% (w/v)

| Ingredient | Quantity (mg) |
| --- | --- |
| Riluzole | 5 |
| Sorbitol | 400 |
| Magnesium aluminium silicate (Veegum ® HV) | 15 |
| Xanthan gum | 1 |
| Sodium lauryl sulphate | 0.02 |
| PEG 25 cetostearyl ether (Volpo ® CS 25) | 1 |
| Simethicone emulsion | 0.033 |
| Sodium saccharine | 1 |
| Purified water | q.s. to 1 ml |

Stability: this formulation was found to be chemically and physically stable for at least 1 month at 40° C./75% R.H.

Example 11

Oral Suspension—Riluzole 0.5% (w/v)

| Ingredient | Quantity (mg) |
| --- | --- |
| Riluzole | 5 |
| Sorbitol | 400 |
| Magnesium aluminium silicate (Veegum ® HV) | 10 |
| Xanthan gum | 1.5 |
| Sodium lauryl sulphate | 0.02 |
| PEG 25 cetostearyl ether (Volpo ® CS 25) | 1 |
| Simethicone emulsion | 0.033 |
| Sodium saccharine | 1 |
| Purified water | q.s. to 1 ml |

Stability: this formulation was found to be chemically and physically stable for at least 1 month at 40° C./75% R.H.

Example 12

Oral Suspension—Riluzole 0.5% (w/v)

| Ingredient | Quantity (mg) |
| --- | --- |
| Riluzole | 5 |
| Sorbitol | 400 |
| Magnesium aluminium silicate (Veegum ® HV) | 10 |
| Xanthan gum | 1 |
| Sodium lauryl sulphate | 0.02 |
| PEG 25 cetostearyl ether (Volpo ® CS 25) | 1 |
| Simethicone emulsion | 0.033 |
| Sodium saccharine | 1 |
| Benzyl Alcohol | 5 |
| Purified water | q.s. to 1 ml |

Stability: this formulation was found to be chemically and physically stable for at least 1 month at 40° C./75% R.H.

Example 13

Oral Suspension—Riluzole 2.75% (w/v)

| Ingredient | Quantity (mg) |
| --- | --- |
| Riluzole | 27.5 |
| Sodium Benzoate | 1.1 |
| Sodium Saccharine | 1.1 |
| Xanthan Gum | 2.75 |
| HPMC | 2.75 |
| Sodium lauryl sulphate | 0.11 |
| Sodium Docusate | 0.275 |
| Simethicone emulsion | 0.11 |
| Purified water | q.s. to 1 ml |

Stability: this formulation proved to be physically and chemically stable for at least 1 week at 40° C.

Example 14

Oral Suspension—Riluzole 2.75% (w/v)

| Ingredient | Quantity (mg) |
| --- | --- |
| Riluzole | 27.5 |
| Methyl paraben | 1.485 |
| Propyl paraben | 0.165 |
| Sorbitol | 440 |
| Magnesium aluminium silicate (Veegum ® K) | 11 |
| NaCMC | 2.2 |
| Sodium lauryl sulphate | 0.11 |
| PEG 25 cetostearyl ether (Volpo ® CS 25) | 0.11 |
| Simethicone emulsion | 0.11 |
| Purified water | q.s. to 1 ml |

Stability: this formulation was found to be chemically and physically stable for at least 1 month at 40° C./75% R.H.

Example 15

The palatability of riluzole suspensions (Examples 6 and 7) was evaluated against riluzole aqueous solutions containing parabens, mint flavor and polyoxyethylene castor oil derivative (Cremophor® RH40) as solubilizer. Placebo was also included in the study, having the composition of Example 7, except for riluzole.

Samples of each composition were evaluated in blind by three scientists (herein referred to as "panelists") according to the following cross-over protocol:

Samples were prepared by an independent scientist, thus panelists did not know what they were asked to taste.

Each panelist was given 2 mL or 10 mL each of test product (corresponding to 50 mg of riluzole). The administered volume was swished in the mouth for about 5 seconds, then expelled from the mouth.

A first evaluation was made during swishing, based on the general "mouth feel" (i.e., attributes such as sweetness, bitterness, astringent, etc.). An evaluation of the aftertaste was then made, based on mouth feeling, mouth irritation, and anaesthetic effects. An arbitrary four-point scale was used (0 through 3), with "0" meaning no anaesthetic effect and "3" indicating the strongest anaesthetic effect. The time required for the anaesthetic effect to disappear was recorded.

Panelists were not allowed to use spring water to rinse their mouth for at least 30 minutes after expelling the sample.

A 1 hour washout period was provided between samples. No more than 4 samples per day were evaluated by each panelist.

Results of the study can be summarized as follows:

2.5% riluzole suspension: good general mouth feel, mild mouth irritation, mild anaesthetic effect, persisting for about 15 minutes.

2.5% riluzole solution: poor general mouth feel, with significant mouth irritation, lip burn and anaesthetic effect (level 3), persisting for at least 20-30 minutes, up to a maximum of 60 minutes (in one case).

0.5% riluzole suspension: good general mouth feel, no mouth irritation, very mild or no anaesthetic effect (level 0-1). In two cases panelists could not tell it from placebo.

0.5% riluzole solution: good general mouth feel, mild mouth irritation and anaesthetic effect (level 2), persisting for at least 15-20 minutes.

Placebo: good general mouth feel, no anaesthetic effect (level 0).

These results represent a surprisingly favourable palatability profile for the compositions of the invention by comparison with riluzole solution, indicating a significant advance in the art, especially in providing an effective treatment for amyotrophic lateral sclerosis with potential for a high degree of patient compliance.

Example 16

Comparative Example

Palatability of riluzole suspension of Example 11 was evaluated versus four different riluzole aqueous suspensions (A-D), containing the same riluzole concentration (0.5%).

The composition of said riluzole aqueous solutions is reported below:
A) riluzole suspended in water;
B) riluzole suspended in water containing 1% of sodium carboxymethylcellulose (NaCMC);
C) riluzole suspended in water containing 0.5% of methylcellulose (MC); and
D) a suspension as described in example 11, where magnesium aluminium silicate and xanthan gum are substituted by 1% sodium carboxymethylcellulose (NaCMC).

Samples of each suspensions were evaluated in blind by three scientists (herein referred to as "panelists") according to the same cross-over protocol reported on example 15.

Results of the study can be summarized as follows:

Example 11: good general mouth feel, no mouth irritation, very mild or no anaesthetic effect (level 0-1).

Suspension A): poor general mouth feel, with significant mouth irritation, anaesthetic effect (level 2-3), persisting for 30-40 minutes.

Suspension B): poor general mouth feel, mild mouth irritation and significant anaesthetic effect (level 2-3), persisting for 30-40 minutes.

Suspension C): poor general mouth feel, mild mouth irritation and anaesthetic effect (level 2-3), persisting for 30-40 minutes.

Suspension D): good general mouth feel, mild mouth irritation, lip burn and anaesthetic effect (level 2-3), persisting for 30-40 minutes.

These results represent a surprisingly favourable palatability profile for the suspension of the invention by comparison with the different four riluzole suspensions, indicating a significant advance in the art, especially in providing an effective treatment for amyotrophic lateral sclerosis with potential for a high degree of patient compliance Moreover, none of the four comparison suspensions showed adequate physical stability for an industrial preparation.

The invention claimed is:

1. An aqueous oral suspension which comprises riluzole or a pharmaceutically acceptable salt thereof, a mixture of at least an anionic surfactant and at least a non-ionic surfactant, and at least a suspending agent comprising magnesium aluminum silicate in an amount from about 0.2% to about 5.0% w/v and xanthan gum in an amount from about 0.1% to about 3.0% w/v, wherein said anionic surfactant is sodium lauryl sulphate present in an amount of from about 0.0001% to about 1% w/v, and said non-ionic surfactant is a polyethyleneglycol ether and wherein riluzole or said pharmaceutically acceptable salt thereof is present in an amount from about 0.1% to about 20% w/v.

2. The suspension according to claim 1, wherein riluzole or said pharmaceutically acceptable salt thereof is present in an amount of from about 0.2% to about 10% w/v.

3. The suspension according to claim 1, wherein riluzole or said pharmaceutically acceptable salt thereof is in particle form.

4. The suspension according to claim 3, wherein the average size of the particles of riluzole or said pharmaceutically acceptable salt thereof is lower than 200 μm.

5. The suspension according to claim 4, wherein said average particle size is from about 75 μm to about 25 μm.

6. The suspension according to claim 1, wherein said mixture of at least an anionic surfactant and at least a non-ionic surfactant is present in amounts from about 0.005% to about 2% w/v.

7. The suspension according to claim 1, wherein riluzole or said pharmaceutically acceptable salt thereof is present in an amount lower than 1.0% w/v.

8. The suspension according to claim 1, wherein riluzole or said pharmaceutically acceptable salt thereof is present in an amount lower than 10% w/v.

9. A method of treating amyotrophic lateral sclerosis in a patent in need of such treatment, said method comprising administering to said patient an effective amount of a suspension according to claim 1.

10. The suspension according to claim 2, wherein riluzole or said pharmaceutically acceptable salt thereof is present in an amount of from about 0.3% to about 6% w/v.

11. The suspension according to claim 4, wherein said average particle size is from about 50 μm to about 10 μm.

12. The suspension according to claim 6, wherein said mixture of at least an anionic surfactant and at least a non-ionic surfactant is present in amounts from about 0.01% to about 0.5% w/v.

13. The suspension according to claim 1, wherein said sodium lauryl sulphate is present in an amount of from about 0.0005 to about 0.5% w/v.

14. The suspension according to claim 1, wherein said sodium lauryl sulphate is present in an amount of from about 0.001 to about 0.1% w/v.

15. The suspension according to claim 7 wherein riluzole or said pharmaceutically acceptable salt thereof is present in an amount of from 0.3% to 0.8% w/v.

16. The suspension according to claim 8, wherein riluzole or said pharmaceutically acceptable salt thereof is present in an amount lower than 5% w/v.

17. The suspension according to claim 8, wherein riluzole or said pharmaceutically acceptable salt thereof is present in an amount from about 0.3% to about 4.0% w/v.

18. The suspension according to claim 1, wherein said polyethylenglycol ether is PEG 25 cetostearyl ether.

* * * * *